(12) United States Patent
Scholten et al.

(10) Patent No.: US 9,566,077 B2
(45) Date of Patent: Feb. 14, 2017

(54) PNEUMATICALLY ACTUATABLE SURGICAL INSTRUMENT

(71) Applicant: Aesculap AG, Tuttlingen (DE)

(72) Inventors: Thomas Scholten, Tuttlingen (DE); Dieter Weisshaupt, Immendingen (DE); Markus Nesper, Tuttlingen (DE); Peter Schulz, Loeffingen (DE)

(73) Assignee: Aesculap AG, Tuttlingen (DE)

( * ) Notice: Subject to any disclaimer, the term of this patent is extended or adjusted under 35 U.S.C. 154(b) by 41 days.

(21) Appl. No.: 14/591,987

(22) Filed: Jan. 8, 2015

(65) Prior Publication Data

US 2015/0157336 A1 Jun. 11, 2015

Related U.S. Application Data

(63) Continuation of application No. PCT/EP2013/065615, filed on Jul. 24, 2013.

(30) Foreign Application Priority Data

Aug. 8, 2012 (DE) ........................ 10 2012 107 292

(51) Int. Cl.
*A61B 17/32* (2006.01)
*A61B 17/16* (2006.01)
A61B 17/00 (2006.01)

(52) U.S. Cl.
CPC ........ *A61B 17/1611* (2013.01); *A61B 17/1604* (2013.01); *A61B 2017/00548* (2013.01)

(58) Field of Classification Search
CPC .................. A61B 17/1604; A61B 2017/00548
See application file for complete search history.

(56) References Cited

U.S. PATENT DOCUMENTS

| | | | |
|---|---|---|---|
| 393,501 A | 11/1888 | Delafield | |
| 3,643,851 A * | 2/1972 | Green | A61B 17/0684 227/120 |
| 3,662,939 A | 5/1972 | Bryan | |
| 3,815,476 A | 6/1974 | Green et al. | |
| 3,837,555 A | 9/1974 | Green | |
| 3,983,947 A | 10/1976 | Wills et al. | |
| 4,063,317 A | 12/1977 | Santore | |
| 4,331,277 A * | 5/1982 | Green | A61B 17/0684 227/130 |
| 4,709,697 A | 12/1987 | Muller | |

(Continued)

FOREIGN PATENT DOCUMENTS

| | | |
|---|---|---|
| DE | 3148619 | 9/1985 |
| DE | 698 14 004 | 7/1994 |

(Continued)

*Primary Examiner* — Zade Coley
(74) *Attorney, Agent, or Firm* — Lipsitz & McAllister, LLC

(57) ABSTRACT

In a pneumatically actuatable surgical instrument comprising a handle and a pressurized gas operated tool arranged at the handle, a replaceable pressurized gas reservoir and a locking device for fixing the pressurized gas reservoir on the handle in an operative position in which the pressurized gas reservoir is connected to a pressurized gas channel by which the tool is supplied with pressurized gas, it is proposed, in order to improve the handling of the pressurized gas reservoir, that the instrument further comprises an unlocking device for releasing the fixing of the pressurized gas reservoir in the operative position.

15 Claims, 6 Drawing Sheets

(56) References Cited

U.S. PATENT DOCUMENTS

| | | | |
|---|---|---|---|
| 4,938,408 A * | 7/1990 | Bedi | A61B 17/072 227/130 |
| 4,951,861 A | 8/1990 | Schulze et al. | |
| 4,964,559 A | 10/1990 | Deniega et al. | |
| 5,018,657 A | 5/1991 | Pedlick et al. | |
| 5,364,001 A * | 11/1994 | Bryan | A61B 17/072 227/175.1 |
| 5,397,046 A | 3/1995 | Savage et al. | |
| 5,399,159 A * | 3/1995 | Chin | A61M 13/003 604/244 |
| 6,619,529 B2 | 9/2003 | Green et al. | |
| 6,786,379 B2 | 9/2004 | Largo | |
| 7,431,189 B2 | 10/2008 | Shelton, IV et al. | |
| 7,441,684 B2 | 10/2008 | Shelton, IV et al. | |
| 7,448,525 B2 | 11/2008 | Shelton, IV et al. | |
| 7,578,311 B2 | 8/2009 | Zaiser et al. | |
| 7,845,532 B2 | 12/2010 | Burke et al. | |
| 8,567,302 B2 | 10/2013 | Scholten et al. | |
| 2004/0230157 A1 | 11/2004 | Perry et al. | |
| 2006/0069395 A1 | 3/2006 | Lebet | |
| 2006/0112944 A1 | 6/2006 | Su | |
| 2006/0151567 A1 | 7/2006 | Roy | |
| 2007/0213769 A1 * | 9/2007 | Schulz | A61B 17/1611 606/219 |
| 2008/0029570 A1 | 2/2008 | Shelton et al. | |
| 2008/0029571 A1 | 2/2008 | Shelton et al. | |
| 2008/0029572 A1 | 2/2008 | Shelton et al. | |
| 2008/0029573 A1 | 2/2008 | Shelton et al. | |
| 2008/0029575 A1 * | 2/2008 | Shelton | A61B 17/068 227/176.1 |
| 2008/0029576 A1 * | 2/2008 | Shelton | A61B 17/07207 227/176.1 |
| 2008/0029577 A1 * | 2/2008 | Shelton | A61B 17/068 227/176.1 |
| 2008/0135598 A1 * | 6/2008 | Burke | B25C 1/047 227/130 |
| 2008/0251569 A1 | 10/2008 | Smith et al. | |
| 2008/0296346 A1 | 12/2008 | Shelton, IV et al. | |
| 2008/0300580 A1 | 12/2008 | Shelton, IV et al. | |
| 2009/0209990 A1 | 8/2009 | Yates et al. | |
| 2011/0224654 A1 | 9/2011 | Schulz et al. | |
| 2012/0180471 A1 * | 7/2012 | Scholten | A61B 17/068 60/415 |
| 2013/0150854 A1 * | 6/2013 | Scholten | A61B 17/1611 606/79 |

FOREIGN PATENT DOCUMENTS

| | | |
|---|---|---|
| DE | 203 18 275 | 3/2004 |
| DE | 202006008404 | 8/2006 |
| DE | 20 2007 006 801 | 8/2007 |
| DE | 20 2010 003 854 | 10/2010 |
| DE | 10 2010 012 011 | 9/2011 |
| EP | 1 884 205 | 2/2008 |
| IE | 102006024759 | 1/2008 |
| JP | 2009045429 | 3/2009 |
| WO | WO 2009/109198 | 9/2009 |

* cited by examiner

PNEUMATICALLY ACTUATABLE SURGICAL INSTRUMENT

This application is a continuation of international application number PCT/EP2013/065615 filed on Jul. 24, 2013 and claims the benefit of German application number 10 2012 107 292.2 filed on Aug. 8, 2012, which are incorporated herein by reference in their entirety and for all purposes.

BACKGROUND OF THE INVENTION

The invention relates to a pneumatically actuatable surgical instrument comprising a handle, a pressurized gas operated tool arranged at the handle, a replaceable pressurized gas reservoir and a locking device for fixing the pressurized gas reservoir on the handle in an operative position in which the pressurized gas reservoir is connected to a pressurized gas channel by which the tool is supplied with pressurized gas.

The pneumatically actuatable surgical instruments described at the outset often receive their supply of pressurized gas from pressurized gas reservoirs in the form of pressurized gas cartridges so that the need for connecting the instrument to a pressurized gas hose for its supply with pressurized gas can be dispensed with and maximum ease of handling of the surgical instrument is achieved.

A problem with the pneumatically operated instruments that are equipped with a pressurized gas reservoir is that when a pressurized gas reservoir has reached the end of its useful life, it always contains a residual volume of pressurized gas and this will escape with a loud explosive sound at the time of removing the pressurized gas reservoir from the instrument.

Pneumatically operated instruments constructed in accordance with the invention and comprising a pressurized gas reservoir are often employed in difficult interventions on the central nervous system. Examples of such instruments include pneumatically operated bone punches which permit the removal of bone or tissue material from a patient by applying a large force.

If the surgeon is still occupied with a difficult procedure and the replacement of a pressurized gas cartridge of a pneumatically operated instrument is going on in the background, the surgeon can easily be startled into uncontrollable reactions.

In pneumatically operated bone punches it is of particular importance for the punching force not to decline during the intervention on the patient because otherwise, in the intervention on the patient, the shaft may stay fixed at the bone, while on the other hand the force of the punch no longer suffices to cut through the bone material. Therefore, in this kind of pneumatically operated bone punches the function of the bone punch is automatically limited when pressure reaches or falls below a minimum value.

As a consequence of this, the pressurized gas reservoir has considerable amounts of pressurized gas left inside; here the remaining pressurized gas pressure is for example approximately 2 bar, which is a pressure sufficient to produce an explosive sound of varying degrees of loudness every time the pressurized gas reservoir is replaced.

On the other hand, if the pneumatically operated instrument and the pressurized gas reservoir arranged therein had not been made use of extensively during surgery, it may also be that at the end of surgery the pressurized gas reservoir is still almost full. However, to allow for further use, the instrument then must be reconditioned and this inevitably requires the pressurized gas cartridge to be removed. Here the pressure remaining in the pressurized gas reservoir is even much higher and here as well it is important that removing the pressurized gas reservoir poses no danger to the staff.

SUMMARY OF THE INVENTION

It is an object of the present invention to make the pneumatically actuatable instrument described at the outset simpler and safer in the handling of the pressurized gas reservoir.

This object is achieved by a pneumatically actuatable surgical instrument having the features of claim 1.

An essential feature of the present invention is that the pressure reservoir cannot be readily removed from the instrument but rather requires the unlocking device to be actuated first before the pressurized gas reservoir can then in a subsequent step, upon release of the fixing of the pressurized gas reservoir in the operative position, be released and replaced.

Preferably, the unlocking device comprises a vent device which upon actuation of the unlocking device is activated and transferred from a rest position to a first operative position in which the pressurized gas channel is connected to a vent opening. In a variant of the present invention, the pressurized gas reservoir can then be released and separated from the instrument and replaced.

In a further variant, provision is made for the vent device, when in its first operative position, not to release the pressurized gas reservoir yet but rather to continue blocking it until the unlocking device is moved to a second operative position in which the pressurized gas channel is still connected to the vent opening. In this variant, it is only in the second operative position that the pressurized gas reservoir is released for separation from the instrument.

Irrespective of the amount of residual pressure remaining in the pressurized gas reservoir, this provision provides for adequate pressure reduction, i.e., emptying of the pressurized gas reservoir, to take place before the unlocking device is transferred to the second operative position and the pressurized gas reservoir can be separated from the instrument. Faulty operation when replacing the pressurized gas reservoir is therefore prevented.

The use of an unlocking device which in a preferred variant of the present invention comprises a vent device makes possible controlled venting of the pressurized gas reservoir so that momentary venting of the pressurized gas reservoir, accompanied by an explosive sound, is omitted.

In pressurized gas reservoirs that are equipped with a screwed connection, a certain remedy could be provided by extending the thread length so that removal of the pressurized gas reservoir is for example only possible by making a plurality of 360° turns so that in the process of removing the pressurized gas reservoir from the surgical instrument, after separating the pressurized gas reservoir from the pressurized gas channel of the instrument, there is enough time left for pressure to reduce while the pressurized gas reservoir is, at its threaded section, still held in engagement with the handle and the mating thread of the handle.

However, this approach does not force the user first to effect the unlocking in a prior step and only then to initiate the actual step of replacing the pressurized gas reservoir. Also, controlled venting is not possible and unscrewing the pressurized gas reservoir from the surgical instrument would not be an easy task to handle. In particular, replacement of the pressurized gas reservoir would be a time-consuming process.

By contrast, the pneumatically actuatable surgical instrument constructed in accordance with the invention can be supplied with a new pressurized gas cartridge more quickly and more easily in terms of handling; in particular, a preferred embodiment provides for the excess pressurized gas to be exhausted from the instrument via a vent in a predetermined direction, as will be described below.

Even though the surgical instrument constructed in accordance with the invention in a preferred variant thereof precludes the pressurized gas reservoir from being separated from the instrument without controlled venting, this function can be implemented without making the handling of the instrument more complicated, in particular without adding weight to the instrument and without making it more costly to manufacture.

In particular, the pneumatically actuatable surgical instrument can also be combined with a bayonet mounting for the pressurized gas reservoir in which the process of dismounting consists of a simple 120° twist and is therefore very quick to carry out without compromising safety when replacing the pressurized gas reservoir.

For the reasons mentioned at the outset it is advantageous for the surgical instrument constructed in accordance with the invention to be equipped with a pressure sensor for monitoring the pressure inside the pressurized gas reservoir. This is preferably implemented by way of monitoring the operating pressure inside the pressurized gas channel leading to the tool.

In addition, it is advantageous for the instrument to comprise an indicating device for indicating the current fill state of the pressurized gas reservoir, and such indicating device may likewise be coupled to the operating pressure inside the pressurized gas channel so that the surgeon utilizing the instrument is always aware of the fill state of the pressurized gas reservoir. In particular, this provides a way of indicating to the surgeon that the supply of pressurized gas contained in the pressurized gas reservoir is too low for further use of the pneumatically operated instrument, enabling the surgeon to identify immediately the reason for the blocked function of the pneumatic instrument.

In a particularly advantageous embodiment of the pneumatically operated instrument, provision is made for the locking device and the unlocking device to be configured as one mechanical unit. This simplifies the processes of inserting and separating the pressurized gas reservoir in and from the instrument.

This mechanical unit comprising the locking device and the unlocking device may additionally have integrated therein an indicating device for indicating the current fill state of the pressurized gas reservoir so that all of the three functions of locking, unlocking and fill state indication can be performed by one mechanical unit. This is advantageous in terms of fabrication and, moreover, provides ease of handling and can additionally be used as a sensory notification of the current fill state of the pressurized gas reservoir so that the surgeon can be given notification of the current fill state without him/her having visual contact with the indicating device.

In a particularly preferred embodiment of the surgical instrument constructed in accordance with the invention, provision is made for the unlocking device to be movable from the rest position to the first operative position and the second operative position by use of a single actuating element.

This simplifies handling of the surgical instrument considerably when replacing the pressurized gas reservoir, with the safety for the unlocking process being given by the actuating element being capable of being moved to a second operative position via a first operative position in which venting already occurs.

The hissing noise that occurs when venting provides the user with feedback on the progression of the emptying of the pressurized gas reservoir.

More preferably, the surgical instrument constructed in accordance with the invention comprises an exhaust channel that receives spent pressurized gas from the tool and exhausts same to the environment. This applies on the one hand to the regular operation of the surgical instrument and it can more preferably also be used for discharging the residual pressurized gas from the pressurized gas reservoir when the latter is replaced, by the vent opening being in fluid communication with the exhaust channel or by it being placed in fluid communication with the exhaust channel during the process of unlocking.

Further reduction of the generation of noise when replacing the pressurized gas reservoir can be achieved by providing either the vent opening or the exhaust channel itself with a silencer.

In a more preferred embodiment of the surgical instrument constructed in accordance with the invention, provision is made for the locking device to be capable of being pneumatically activated, in particular by the pressurized gas of the pressurized gas reservoir.

In this way, the locking device does not become active before the pressurized gas reservoir is in fluid communication with the pneumatic unit of the instrument, and it is not until this condition has been reached that locking of the pressurized gas reservoir is required. In the case of improper installation of the pressurized gas reservoir, wherein the latter does not fluidly communicate with the pneumatic device of the instrument at all, this prevents premature locking and the associated more complicated correction of the position of the installed pressurized gas reservoir.

In accordance with a variant of the surgical instrument constructed in accordance with the invention, the pressurized gas reservoir is held at the handle of the instrument directly. This can be accomplished as described in US 2006/0151567 A, for example.

In another alternative, provision is made for the pressurized gas reservoir to be held in a housing at the handle of the instrument. Examples of such arrangements may be found in DE 20 2007 006 801 U1 as well as in US 2006/0151567 A. Here, the housing is configured as part of the handle. Alternatively, the housing may in accordance with the invention also be configured as a separate part and capable of being removably attached to the handle of the instrument.

More preferably, surgical instruments constructed in accordance with the invention comprise a detector which checks for and optionally also indicates the presence of a pressurized gas reservoir in the operative position at the handle of the instrument.

Preferably, the surgical instrument constructed in accordance with the invention comprises a sensing device with which the engagement of the pressurized gas reservoir can be detected.

In particular, the sensing device may be equipped with a mechanical or optical sensor.

It is also possible to sense the optional pressure reservoir housing or a pressure reservoir receiver, together with which the pressure reservoir may optionally be mounted to the handle.

Preferably, the pressurized gas reservoir itself is sensed. The sensing operation can be performed either at the outer circumference of the substantially cylindrical pressurized gas reservoir, at the end face thereof or optionally at the area of a shoulder of the pressurized gas reservoir's end which typically narrows like a bottleneck and with which the pressurized gas reservoir is connected to the pressurized gas channel of the instrument.

Preferred mechanical sensors are pin-like sensing elements or hollow-cylindrical elements. The pin-like sensing elements effect contact with a point surface of the pressurized gas reservoir, be it on the outer circumference, the end face or the shoulder area thereof.

The hollow-cylindrical sensing elements, which may be in the shape of a full cylinder or a partial cylinder, typically effect contact with an annular surface in the area of the end face or shoulder of the pressurized gas reservoir.

However, pin-like or hollow-cylindrical sensing elements may also be used for sensing an optional pressurized gas reservoir housing, holder, sleeve or the like.

It is also conceivable for the pin-like or hollow-cylindrical sensing elements to engage an adaptor element with which the pressurized gas reservoir is provided before it is connected to the handle and the pressurized gas channel thereof.

Moreover, it is conceivable to sense a closure element of a pressurized gas reservoir housing into which the pressurized gas reservoir can be inserted before it is connected to the pressurized gas channel of the handle.

Locking the pressurized gas reservoir in the operative position thereof is preferably accomplished by a mechanical locking element.

Preferably, the mechanical locking element in its active position engages in a recess provided on the pressurized gas reservoir itself, the housing thereof or other holder, a closure element of the housing or of the holder or in a locking mechanism for such a housing, holder or of the closure element.

Locking via the mechanical locking element is preferably effected pneumatically by the gas pressure delivered by the pressurized gas reservoir and is more preferably effected against the force exerted by a resilient element. Once the pressure provided by the pressurized gas reservoir has decreased below a predetermined value, the locking element is transferred from its active position to a non-active position and the pressurized gas reservoir is released for removal.

More preferably, the surgical instrument comprises a control device which enables the function of the tool when the gas pressure inside the pressurized gas reservoir is at a predetermined sufficient level and disables the function of the tool when the gas pressure is too low. Surgical instruments of this type may in particular be configured and used as bone punches.

These and further advantages of the invention are described in more detail below with reference to the drawings and a preferred exemplary embodiment.

DETAILED DESCRIPTION OF THE INVENTION

Figure 1:
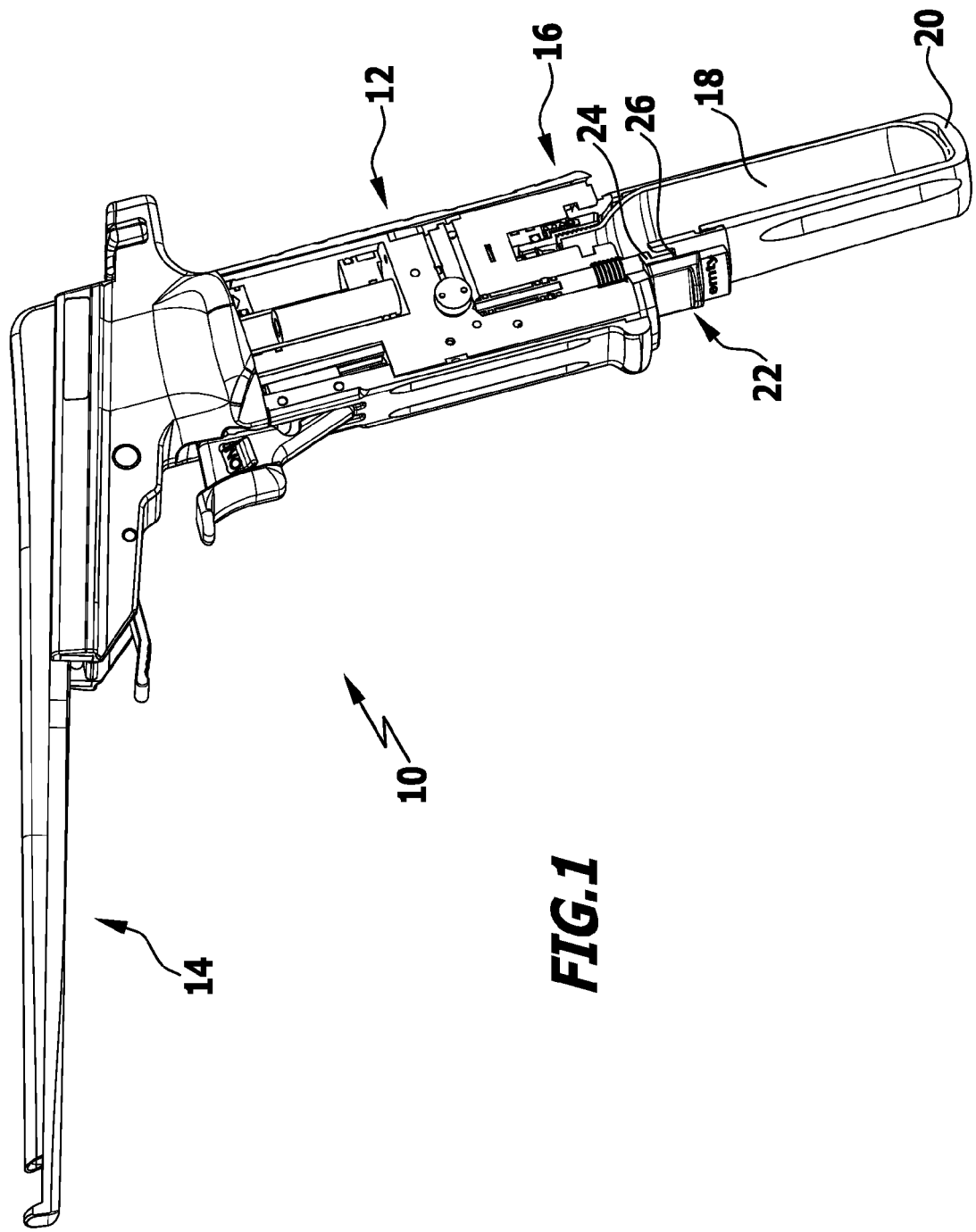
FIG. 1 is a partially broken away view of a pneumatically operated surgical instrument constructed in accordance with the invention, illustrated as being in the form of a bone punch.

FIG. 1 shows an instrument constructed in accordance with the invention, said instrument being in the form of a bone punch 10 comprising a handle 12 formed like a pistol grip and a pneumatically operable punching tool 14 held thereon.

At its end spaced apart from the tool 14, the handle 12 has a connecting device 16 by way of which a pressurized gas reservoir 18 is capable of being connected to the handle 12. In the present exemplary embodiment of an instrument 10 constructed in accordance with the invention, the pressurized gas reservoir 18 is mounted to the handle 12 along with a hollow-cylindrical housing part 20 so that the connection between the handle 12, or the pressurized gas channel thereof (not shown here), and the pressurized gas reservoir 18 is protected against mechanical influences.

In the operating condition as depicted in FIG. 1, the pressure inside the pressurized gas reservoir 18 has dropped to such an extent that with the amount of pressure available in the pressurized gas channel, the punching tool 14 can no longer be worked safely and hence the function of the bone punch 10 is blocked. In order to indicate to the staff the reason which caused the punching tool 14 to become blocked, an indicating element 22 is provided on the handle 12, adjacent to the connecting device 16, said indicating element 22 in the present operating condition having the word "empty" released and therefore open to view thereon. Concomitant therewith, a latch element 24 is out of engagement with a recess 26 on the housing part 20, thus enabling the housing part 20 together with the pressurized gas reservoir 18 to be separated from the instrument by rotation of the bayonet closure (not shown in detail here).

As mentioned at the outset, for reasons of safety the function of the bone punch 10 is blocked at a point in time when the pressurized gas reservoir 18 still has a considerable amount of residual pressure inside. To prevent the pressurized gas reservoir 18 and the handle 12 or the pressurized gas channel of the handle 12 from being readily separated from each other while in this state, a latch element 24 still held in an activated position by the residual pressure engages within a recess 26 at the upper circumference 28 of the housing part 20.

Figure 2:
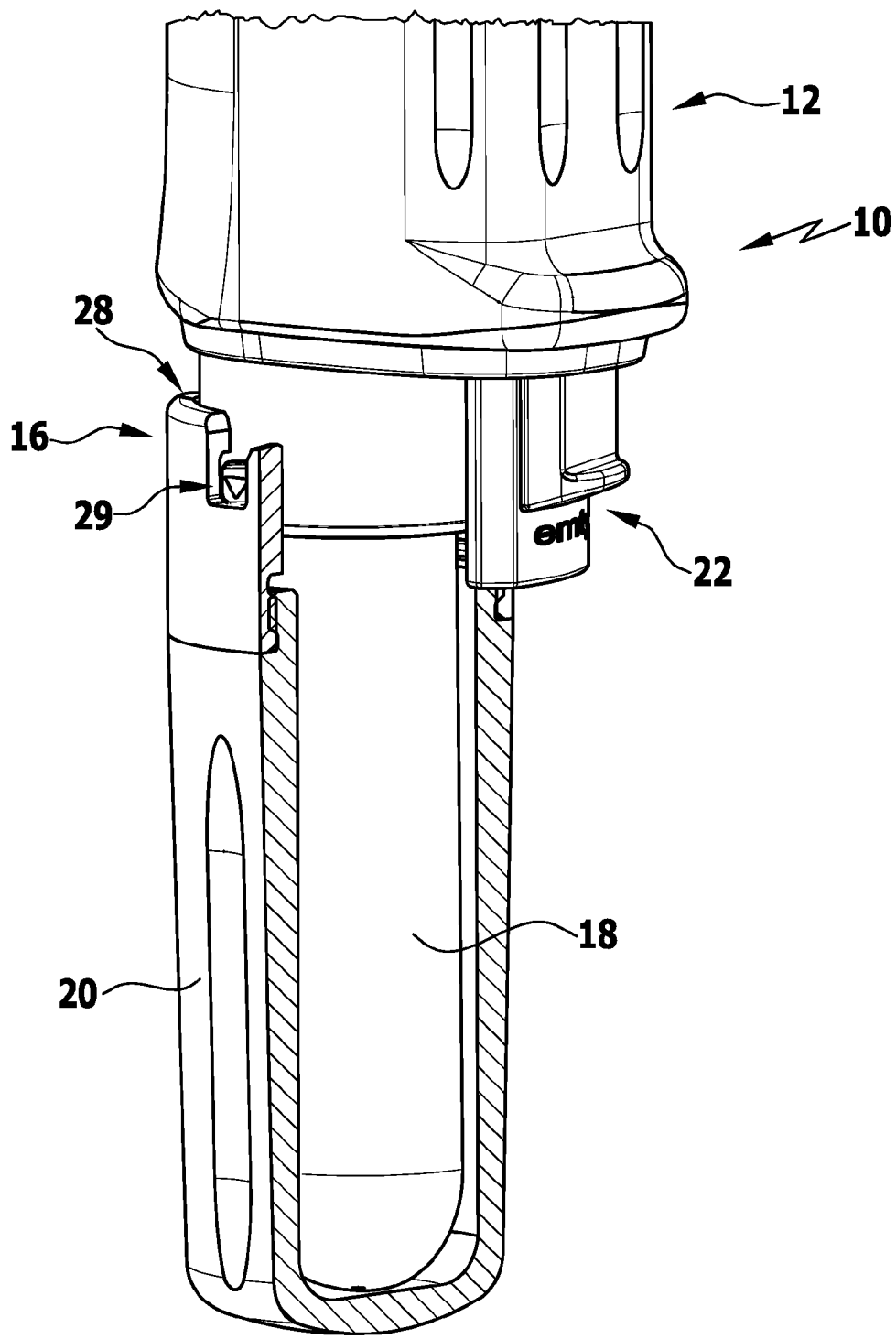
FIG. 2 shows a detail of the bone punch of FIG. 1.

This operating condition is explained in greater detail below with reference to an enlarged detail view of FIG. 2.

In the present exemplary embodiment, the housing part 20 is coupled to the handle 12 or the connecting device 16 thereof by way of a bayonet closure 29, which per se allows quick exchange of the pressurized gas reservoir 18. In the operating condition as illustrated in FIG. 2, the latch element 24 is in a non-active position, in which it is out of engagement with the recess 26; the residual pressure inside the pressurized gas reservoir 18 is reduced to a predetermined value, preferably substantially corresponding to ambient pressure. It is not until this condition has been reached that the bayonet closure can be released by rotational movement thereof and that the housing part 20 together with the pressurized gas reservoir 18 held therein can be separated from the handle 12 and, ultimately, that the pressurized gas reservoir 18 can be replaced.

The procedure for replacing a pressurized gas reservoir 18 will be described in more detail below with reference to FIGS. 3 to 5.

Figure 3:
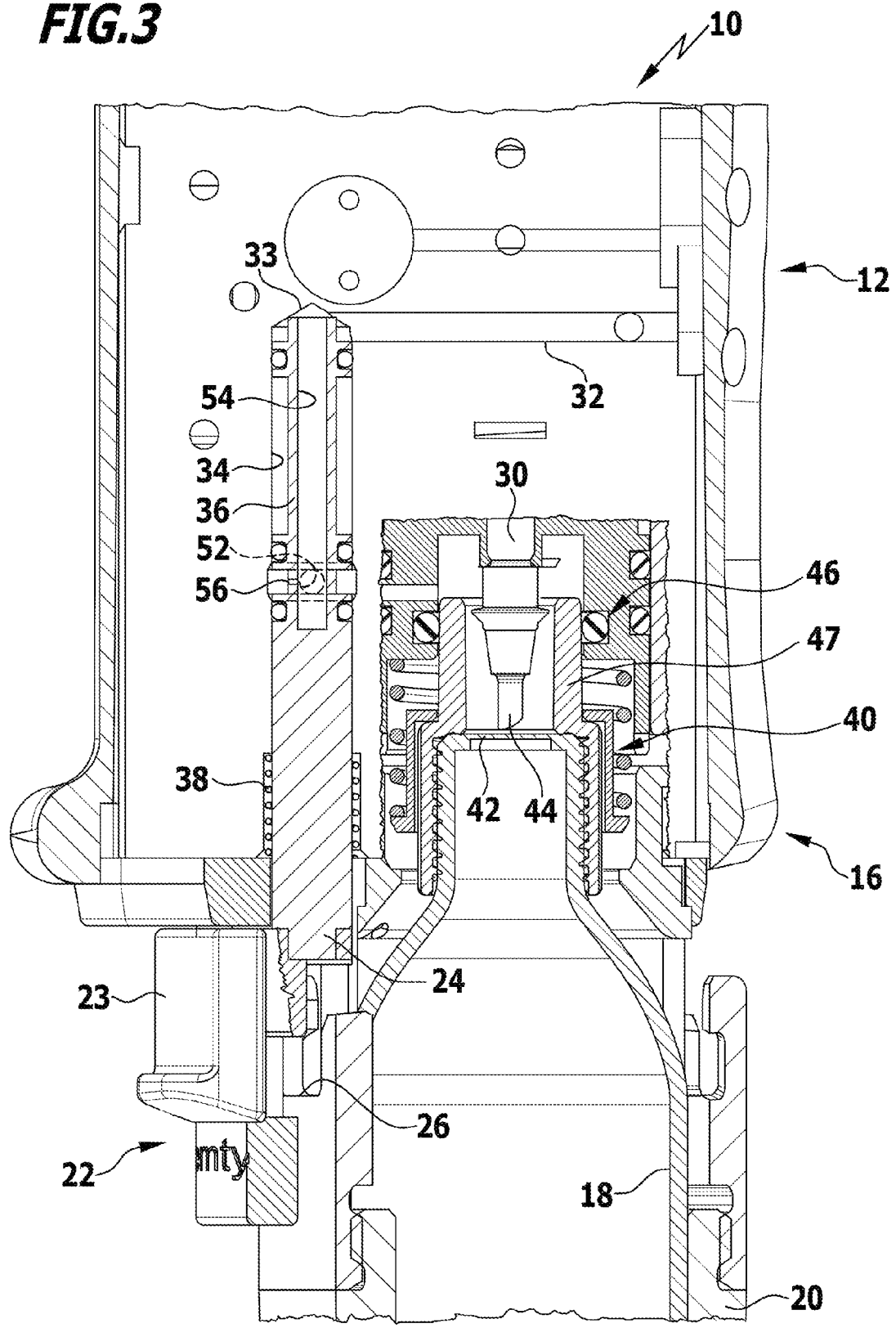
FIGS. 3, 4 and 5 are sectional views of a part of the bone punch of FIG. 1 shown in different operating conditions.

FIG. 3 is a sectional view taken through the connecting device 16 of the handle 12 in an operating condition in which a fresh pressurized gas reservoir 18 is to be connected to the instrument 10. In this condition, the pressurized gas channel 30 of the handle 12 is pressureless. Accordingly, a control channel 32 branching off the pressurized gas channel 30 is also pressureless.

The control channel 32 is connected to the closed end 33 of a cylindrical bore 34 in the handle 12 having mounted therein a control piston 36 for longitudinal displacement therein. With the control channel 32 in the pressureless condition, the control piston 36 is urged against the closed end 33 of the bore 34 by a helical spring 38. The latch element 24, which in the present exemplary embodiment is formed in one piece with the control piston 36, is in its non-active position.

At this point, the housing part 20 together with a fresh pressurized gas reservoir or cartridge 18 arranged therein can be connected to the connecting device 16 of the handle 12 by way of a bayonet closure.

As shown in FIG. 3 the cartridge 18 is in a condition in which the end 40 thereof that has been inserted into the connecting device is still sealed in a gas-tight and pressure-resistant manner with a seal 42.

In the area of the connecting device 16, the pressurized gas channel 30 of the handle 12 terminates in a hollow-cylindrical end 44 that is ground at an oblique angle to the axial direction for piercing the seal 42. The pitch of the bayonet closure is selected such that when the bayonet closure is rotated during closing movement thereof, the housing part 20 causes the cartridge 18 to be engaged so far into the connecting device 16 of the handle 12 that the end 44 passes completely through the seal 42 and penetrates the upper, open end 40 of the cartridge 18. At the same time, the outer circumference of the upper end 40 of the cartridge 18 or, as illustrated in the present exemplary embodiment, an adaptor sleeve 47 screwed onto the cartridge 18 is engaged by a seal 46 arranged in the connecting device so that a gas-tight connection is established between the cartridge 18 and the pressurized gas channel 30. This situation is depicted in FIG. 4.

In this situation, the pressure of the cartridge 18, which is for example approximately 10 to 12 bar, acts through the pressurized gas channel 30 and the control channel 32 on the closed end of the bore 34 and, acting against the force of the spring 38, urges the control piston 36 out of the non-active position thereof. The latch element 24, which is configured in one piece with the control piston 36, engages into the recess 26 of the housing part 20 and blocks the bayonet closure. The instrument 10 is now ready for use. Separating the cartridge 18 from the handle 12 is not possible while in this state.

When, as a result of operating the instrument, the pressure inside the gas cartridge 18 decreases to a predetermined pressure value, for example approximately 2 bar, the control piston 36 is by spring force moved in the bore 34 in a direction towards the closed end 33 of the bore 34. The latch element 24, however, remains in an active position and engages, albeit only partially, within the recess 26 of the housing part 20.

In this operating condition, the tool is blocked in its function and the indicating element is halfway between the two positions "full" and "empty".

Figure 5:
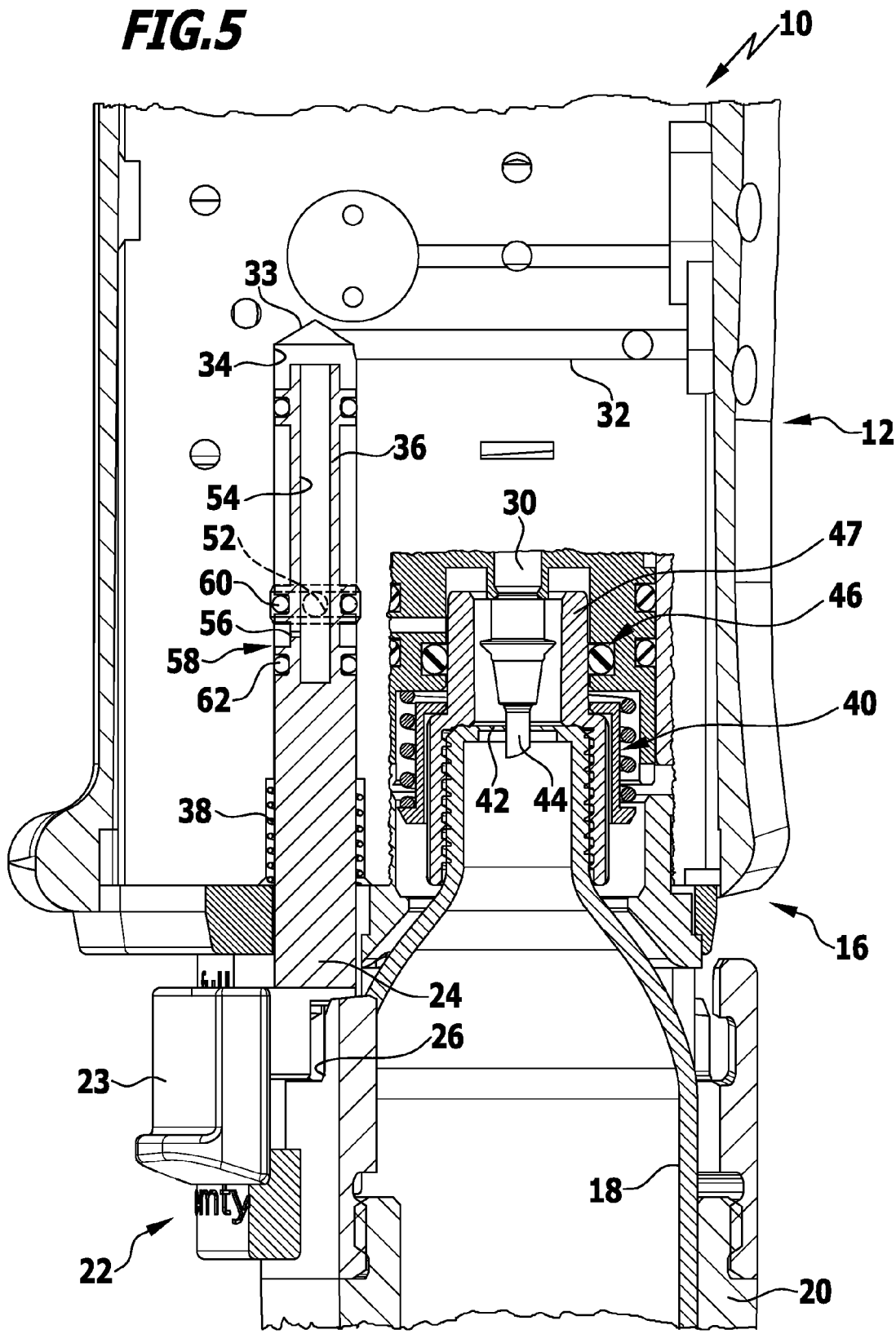
Figure 6A:
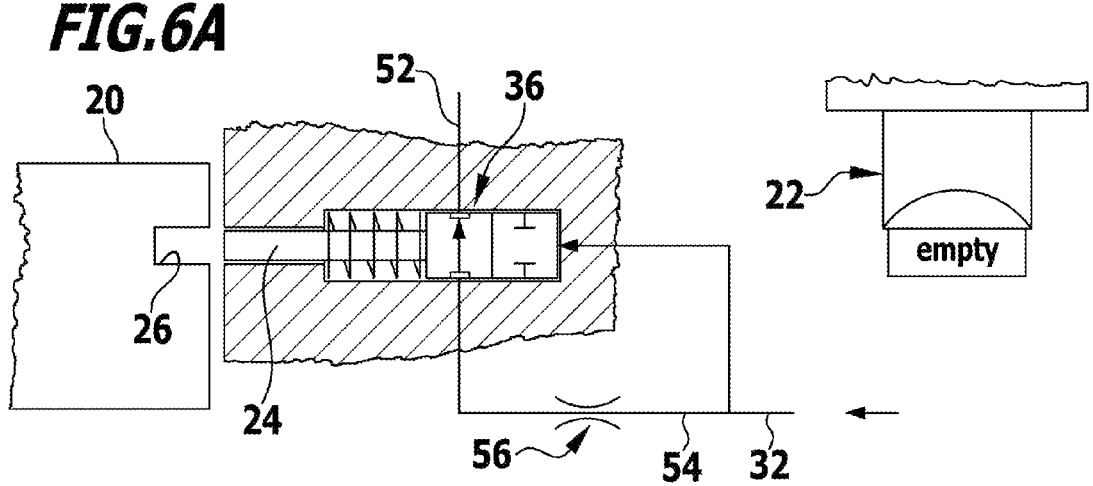
FIGS. 6A to 6C are circuit diagrams of part of the pneumatics employed in the bone punch of FIG. 1, for explaining the operating conditions illustrated in FIGS. 3 to 5.
Figure 6B:
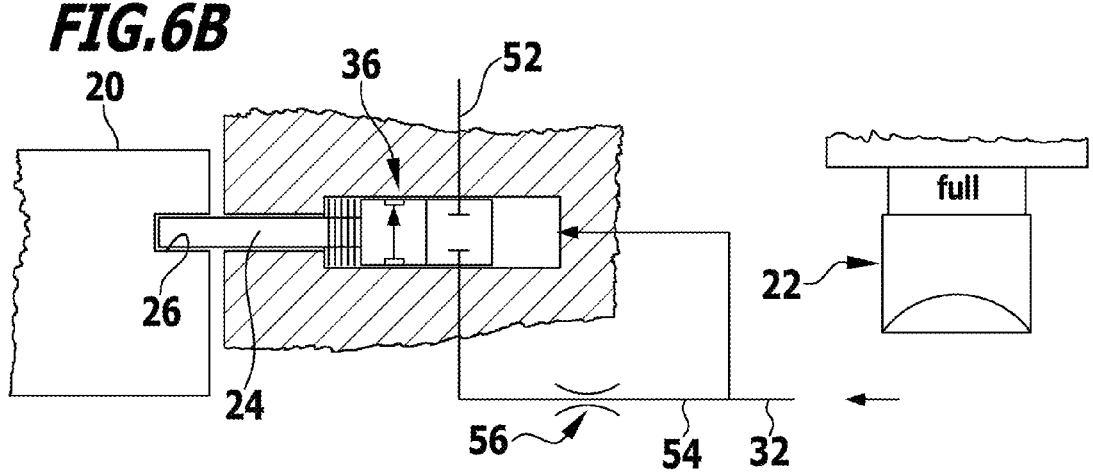
Figure 6C:
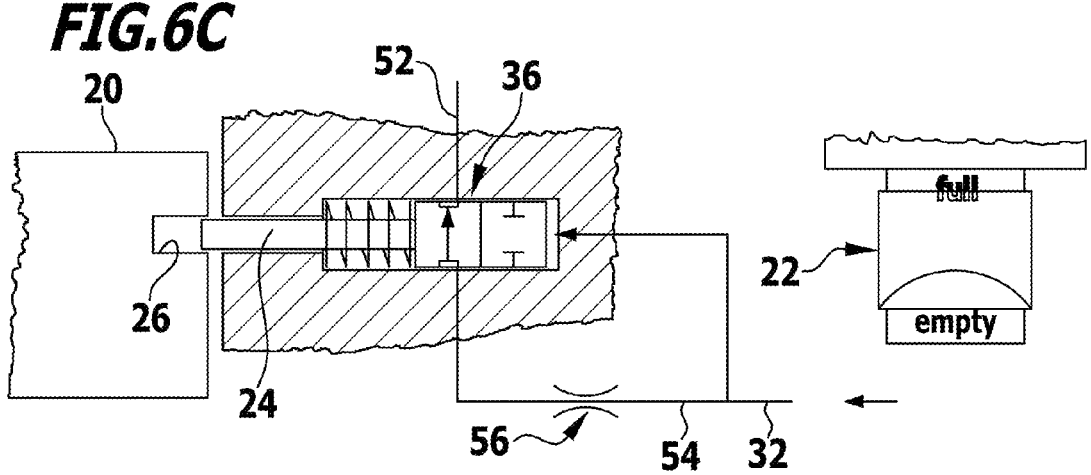

Using the slider 23 arranged on the latch element 24, the control piston 36 can be urged in a direction towards the end position (second operative position of the unlocking device), as is shown in FIG. 3, wherein already in a first operative position of the unlocking device, shown in FIG. 5, connection of the control channel 32 and therefore also of the pressurized gas channel 30 and the gas volume of the cartridge 18 to a vent conduit 52 is established and sustained and the residual pressure inside the gas cartridge 18 can be reduced to ambient pressure.

To this end, the control piston 36 has a central axial bore 54 which is formed as a blind hole extending from the control channel-side end of the control piston 36 in a direction towards the latch element 24. Provided at the closed end of the axial bore 54 is a transverse bore 56 which is configured as a throttle.

Configuring the transverse bore 56 as a throttle prevents any substantial amount of pressurized gas escaping when a fresh cartridge 18 is inserted and connected to the handle 12 and the pressurized gas channel 30 thereof.

At the outer circumference of the control piston 36, the transverse bore 56 terminates in a section 58 which, when viewed in an axial direction, is sealed on either side via seals 60 and 62 respectively against the residual volume of the bore 34. The length of the section 58 in an axial direction of the control piston 36 is dimensioned such that the section 58 is brought into fluid communication with the vent conduit 52 prior to the latch element 24 disengaging completely from the recess 26. In this way, controlled venting of the pressurized gas channel 30 and of the cartridge 18 can be initiated before the housing part 20 can be separated from the handle 12 by way of the bayonet closure.

Figure 4:
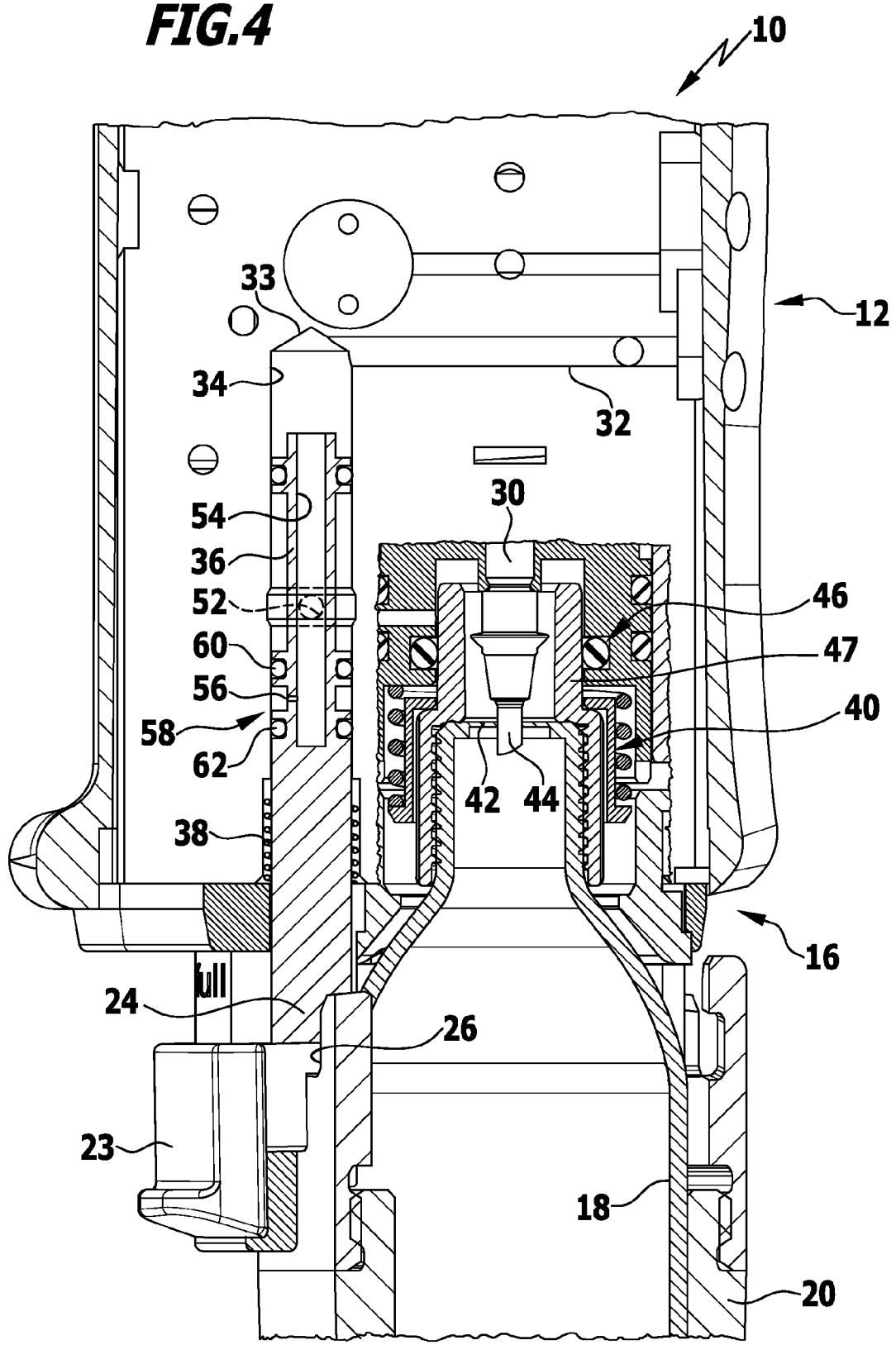

In order to better illustrate the pneumatic switching statuses of FIGS. 3 to 5, FIGS. 6A to 6C show once again the indicating function of the latch element 24/slider 23 together with a circuit diagram, wherein the individual elements are denoted by the same reference numerals as in FIGS. 3 to 5.

What is claimed is:

1. A pneumatically actuatable surgical instrument, comprising:
   a handle,
   a pressurized gas-operated tool arranged at the handle,
   a replaceable pressurized gas reservoir,
   a locking device for fixing the pressurized gas reservoir on the handle in an operative position mechanically preventing removal of the pressurized gas reservoir, the locking device being pneumatically activatable by pressurized gas of the pressurized gas reservoir, and
   an unlocking device for releasing the fixing of the pressurized gas reservoir from the operative position,
   wherein:
   in the operative position, the pressurized gas reservoir is connected to a pressurized gas channel by which the tool is supplied with pressurized gas,
   the unlocking device comprises a vent device which upon actuation of the unlocking device is movable from a rest position to a first operative position in which the pressurized gas channel is connected to a vent opening, and
   the unlocking device is movable from the first operative position to a second operative position in which the locking device is inactive and the pressurized gas reservoir is released for replacement.

2. The surgical instrument in accordance with claim 1, further comprising a pressure sensor for monitoring pressure inside the pressurized gas reservoir.

3. The surgical instrument in accordance with claim 1, further comprising an indicating device for indicating a current fill state of the pressurized gas reservoir.

4. The surgical instrument in accordance with claim 1, wherein the locking device and the unlocking device are configured as one mechanical unit.

5. The surgical instrument in accordance with claim 4, wherein the mechanical unit comprising the locking device and the unlocking device comprises an integrated indicating device for indicating a current fill state of the pressurized gas reservoir.

6. The surgical instrument in accordance with claim 1, wherein the unlocking device is movable from the rest position to the first operative position and the second operative position by use of a single actuating element.

7. The surgical instrument in accordance with claim 1, further comprising an exhaust channel that receives spent pressurized gas from the tool and exhausts the spent pressurized gas to the environment.

8. The surgical instrument in accordance with claim 1, wherein the pressurized gas channel is in fluid communication with the vent opening when in the first operative position and in the second operative position.

9. The surgical instrument in accordance with claim 1, wherein the vent opening or an exhaust channel for spent pressurized gas comprises a silencer.

10. The surgical instrument in accordance with claim 1, wherein the pressurized gas reservoir is held at the handle of the instrument directly.

11. The surgical instrument in accordance with claim 1, wherein the pressurized gas reservoir is held in a housing at the handle of the instrument.

12. The surgical instrument in accordance with claim 1, further comprising a sensor which checks for and indicates a presence of the pressurized gas reservoir when fixed at the handle of the instrument.

13. The surgical instrument in accordance with claim 1, further comprising a control device which enables operation of the tool when a gas pressure inside the pressurized gas reservoir is at a predetermined level and disables operation of the tool when the gas pressure is below the predetermined level.

14. A pneumatically actuatable surgical instrument, comprising:
   a handle,
   a pressurized gas-operated tool arranged at the handle,
   a replaceable pressurized gas reservoir,
   a housing for the pressurized gas reservoir,
   a locking device for fixing the housing on the handle and locking the pressurized gas reservoir in an operative position preventing removal of the pressurized gas reservoir from the handle, and
   an unlocking device for releasing the fixing of the housing and releasing the pressurized gas reservoir from the operative position,
   wherein:
   in the operative position, the pressurized gas reservoir is connected to a pressurized gas channel by which the tool is supplied with pressurized gas,
   the unlocking device comprises a vent device which upon actuation of the unlocking device is movable from a rest position to a first operative position in which the pressurized gas channel is connected to a vent opening,
   the unlocking device is movable from the first operative position to a second operative position in which the locking device is inactive and the pressurized gas reservoir is released for replacement, and
   the locking device comprises a movable slider arranged on the housing which interacts with a corresponding recess in the handle.

15. The surgical instrument in accordance with claim 14, wherein the locking device is pneumatically activatable by the pressurized gas of the pressurized gas reservoir.

\* \* \* \* \*